United States Patent [19]

Akemi et al.

[11] Patent Number: 5,683,710
[45] Date of Patent: Nov. 4, 1997

[54] PERCUTANEOUS ABSORPTION PREPARATION

[75] Inventors: Hitoshi Akemi; Takateru Muraoka; Kazuhiro Higashio; Saburo Otsuka; Takashi Kinoshita, all of Osaka, Japan

[73] Assignees: Nitto Denko Corporation, Osaka; Toa Eiyo Ltd., Tokyo, both of Japan

[21] Appl. No.: 527,535

[22] Filed: Sep. 13, 1995

[30] Foreign Application Priority Data

Sep. 14, 1994 [JP] Japan .................. 6-219888

[51] Int. Cl.⁶ ................................................ A61F 13/02
[52] U.S. Cl. ............................................ 424/448; 424/449
[58] Field of Search ................................. 424/448, 449

[56] References Cited

U.S. PATENT DOCUMENTS

| | | | |
|---|---|---|---|
| 5,204,109 | 4/1993 | Akemi et al. | 424/443 |
| 5,419,912 | 5/1995 | Morimoto | 424/443 |

FOREIGN PATENT DOCUMENTS

| | | | |
|---|---|---|---|
| 0062682 | 10/1982 | European Pat. Off. . | |
| 0436203 | 7/1991 | European Pat. Off. . | |
| 0531938 | 3/1993 | European Pat. Off. . | |
| 3839410 | 6/1989 | Germany . | |
| 57-116011 | 7/1982 | Japan | A61K 9/70 |
| 3-223212 | 10/1991 | Japan | A61K 9/70 |
| 8606281 | 11/1986 | WIPO . | |

*Primary Examiner*—D. Gabrielle Phelan
*Attorney, Agent, or Firm*—Sughrue,Mion,Zinn,Macpeak & Seas, PLLC

[57] ABSTRACT

A percutaneous absorption preparation for use in the administration of isosorbide dinitrate (ISDN) as a coronary vasodilator into the living body by percutaneous absorption, which has excellent adhesion to the skin and does not cause pain and damage to stratum corneum when peeled off, is disclosed. The pressure-sensitive adhesive layer comprises an acrylic copolymer prepared by copolymerization of a monomer mixture comprising a (meth)acrylic acid alkyl ester and a functional monomer as the essential components, a fatty acid ester having a specified number of carbon atoms, a monoglyceride having a specified number of carbon atoms, and ISDN, and the pressure-sensitive adhesive layer is crosslinked. Since its skin adhesive property is improved by the inclusion of the monoglyceride, release of ISDN is improved and the area of the preparation can be decreased.

4 Claims, No Drawings

PERCUTANEOUS ABSORPTION PREPARATION

FIELD OF THE INVENTION

This invention relates to percutaneous absorption preparations, and more particularly to a percutaneous absorption preparation for use in the percutaneous administration of isosorbide dinitrate as a coronary vasodilator, which exerts excellent adhesion of its adhesive member to the skin, does not cause a pain or damage to stratum corneum when stripped from the skin and can effect durable and quick absorption of isosorbide dinitrate into the body.

BACKGROUND OF THE INVENTION

In recent years, various skin adhesive type external preparations such as poultices, tapes and the like have been developed as percutaneous absorption preparations for use in the administration of drugs into the living body through the skin, of which tapes that contain drugs capable of exerting systemic pharmacological actions are particularly worthy of notice.

Under such actual circumstances, a tape preparation has been proposed in JP-A-57-116011 (the term "JP-A" as used herein means an "unexamined published Japanese patent application") and developed, which is now on the market, which contains isosorbide dinitrate (hereinafter referred to as "ISDN") that exerts pharmacological actions as a coronary vasodilator and is known as a preventive medicine of angina pectoris attack. This percutaneous absorption preparation, which is produced by including ISDN in an acrylic pressure-sensitive adhesive, can effect durable absorption of ISDN into the living body through the skin by simply adhering it to the skin, thereby exerting excellent pharmacological actions.

However, being a preparation to be adhered to the skin, it has a possibility of causing an eruption on the adhered area of the skin due to irritation and the like when used for a prolonged period of time. That is, in order to fix securely to the skin area to be applied, a conventional percutaneous absorption preparation generally uses a pressure-sensitive adhesive having relatively strong adhesive property or is entirely overcoated with a pressure-sensitive adhesive sheet having strong adhesive property to fix it to the skin through the adhesive property of the sheet. However, when skin adhesion is increased in such a manner, percutaneous transfer of a drug contained therein will be improved in general, but removal of the preparation by stripping it will cause damage to the corneous cells in the applied area of the skin, thus having a possibility of generating significant skin irritation when the preparation is continuously used for a prolonged period of time repeatedly exchanging it with fresh ones.

In consequence, a so-called gel-like percutaneous absorption preparation has been proposed in JP-A-3-223212, for the purpose of reducing such strong adhesion-induced skin irritation. This preparation in which a relatively large amount of oily liquid components having high compatibility are included in an acrylic pressure-sensitive adhesive layer, in order to provide the pressure-sensitive adhesive layer with a soft feeling of touch, is an epoch-making percutaneous absorption preparation which can reduce skin irritation during its application to the skin due to the soft pressure-sensitive adhesive layer and can be removed smoothly after its use without causing damage to the stratum corneum.

However, since these adhesive type percutaneous absorption preparations are used by adhering them to the skin, it is necessary to maintain a balance of their skin adhesion and skin irritation, while simultaneously exerting proper skin transfer and absorption of a drug contained therein. It therefore is an ultimate future object to develop a percutaneous absorption preparation which can satisfy all of these necessities.

The preparation described in JP-A-3-223212 can exert excellent effects which cannot be found in other conventional percutaneous absorption preparations, but improvement is still required in its skin adhesion. In addition, it is desirable to make the size (area) of each percutaneous absorption preparation as small as possible in order to reduce skin irritation, but this preparation also requires improvement in securing skin adhesion when its area is minimized, as well as in skin transfer and absorption of drugs.

SUMMARY OF THE INVENTION

As a result of further investigations to overcome the above-described problems involved in the prior art, it has been found that, in the case of a percutaneous absorption preparation in which ISDN is used as a drug, the above-described problems can be overcome when specified fatty acid ester and monoglyceride are added as liquid components to an acrylic copolymer in which a (meth)acrylic acid alkyl ester is used as the main monomer, and its pressure-sensitive adhesive layer is crosslinked. The present invention has been accomplished on the basis of this finding.

According to the present invention, there is provided a percutaneous absorption preparation comprising a backing and a pressure-sensitive adhesive layer containing a drug for percutaneous absorption, formed on one side of the backing, wherein the pressure-sensitive adhesive layer comprises an acrylic copolymer prepared by copolymerization of a monomer mixture comprising a (meth)acrylic acid alkyl ester and a functional monomer as the essential components, a fatty acid ester comprising a higher fatty acid having 12 to 16 carbon atoms and a lower monohydric alcohol having 1 to 4 carbon atoms, a monoglyceride comprising a higher fatty acid having 8 to 10 carbon atoms and glycerol, and isosorbide dinitrate as the drug for percutaneous absorption, and the pressure-sensitive adhesive layer is crosslinked.

DETAILED DESCRIPTION OF THE INVENTION

Preferred examples of the backing used in the percutaneous absorption preparation of the present invention are those which do not cause reduction of the content of a fatty acid ester, a monoglyceride and ISDN which are contained in the pressure-sensitive layer due to their permeation through the backing into its back side. Examples of the backing which can be used are single films and laminate films of polyester, nylon, Saran, polyethylene, polypropylene, polyvinyl chloride, ethylene-ethyl acrylate copolymer, polytetrafluoroethylene, Surlyn, metal foil and the like. In order to obtain proper adhesive force (anchoring force) between the backing and the pressure-sensitive adhesive layer, it is preferred to prepare the backing as a laminate of a non-porous plastic film and a porous film made of the above materials. In that case, it is preferred to form the pressure-sensitive adhesive layer on the porous film side.

Examples of the porous film include those which can improve anchoring force with the pressure-sensitive adhesive layer, such as paper, woven fabric, non-woven fabric, mechanically punched sheet and the like, of which paper, woven fabric or non-woven fabric is particularly preferred from the standpoint of easy handling and the like. The porous film may have a thickness of from 10 to 500 μm from the standpoint of anchoring force improvement, flexibility of the preparation as a whole and adhesion handling, or a thickness of from 10 to 200 μm in the case of a thin preparation such as a plaster type or pressure-sensitive tape type preparation. When woven or non-woven fabric is used as the porous film, its basis weight is 5 to 30 g/m², and preferably 6 to 15 g/m².

According to the percutaneous absorption preparation of the present invention, the pressure-sensitive adhesive layer which is formed on one side of the backing has a crosslinked structure, namely a gel form, which contains ISDN, an acrylic copolymer, a fatty acid ester and a monoglyceride as the essential components and possesses proper skin adhesive force and cohesive force. The pressure-sensitive adhesive layer of the present invention shows an adhesive force of 80 to 250 g/24 mm width when measured as its adhesive force to a bakelite plate by a measurement method which will be described hereinafter.

The acrylic copolymer used as the structural component of the pressure-sensitive adhesive layer of the present invention shows compatibility with the fatty acid ester and monoglyceride, and has a proper skin adhesion and a property to maintain shape of the pressure-sensitive adhesive layer. In this connection, generally used rubber-based pressure-sensitive adhesives such as natural rubber, synthetic rubber and the like and silicone-based pressure-sensitive adhesives are not preferred to use in the present invention, because these adhesives have insufficient compatibility with fatty acid esters and monoglycerides, and solubility and releasing property of ISDN therein are significantly low. Also, such pressure-sensitive adhesives are not applicable to the present invention, because they have another problem that it is difficult to adjust quantity of functional groups and the like which take part in the crosslinking reaction and to carry out reproducible crosslinking treatment, in comparison with the acrylic copolymer which can be used in the present invention.

Such an acrylic copolymer can be obtained by using a (meth)acrylic acid alkyl ester usually used in acrylic pressure-sensitive adhesives as the main monomer component, and copolymerizing the same with a functional monomer.

Examples of the (meth)acrylic acid alkyl ester which can be used include (meth)acrylic acid alkyl esters which have straight-chain or branched alkyl groups having 4 to 13 carbon atoms, such as butyl, pentyl, hexyl, heptyl, octyl, nonyl, decyl, undecyl, dodecyl, tridecyl and the like. These esters can be used alone or as a mixture of two or more thereof.

The (meth)acrylic acid alkyl ester is not particularly limited to the above examples, and a (meth)acrylic acid alkyl ester having an alkyl group of 1 to 3 carbon atoms or a (meth)acrylic acid alkyl ester having an alkyl group of 14 or more carbon atoms may be used together so long as it does not alter characteristics of the present invention.

Examples of the functional monomer which can be copolymerized with the (meth)acrylic acid alkyl ester include those which have at least one unsaturated double bond which participates in copolymerization reaction in one molecule, and also have functional groups such as carboxyl, hydroxyl, sulfoxyl, amino, amido, alkoxyl and the like in their side chains. Of these functional monomers, (meth)acrylic acid is particularly preferred in view of adhesive and cohesive properties as pressure-sensitive characteristics, releasing property of ISDN contained in the pressure-sensitive adhesive layer and reactivity when the pressure-sensitive adhesive layer is crosslinked.

When a copolymer of the (meth)acrylic acid alkyl ester and (meth)acrylic acid is used as the optimum acrylic copolymer of the present invention, these monomers may be used in a weight ratio of 90/10 to 99/1, and preferably 92/8 to 97/3.

A fatty acid ester and a monoglyceride to be blended in the pressure-sensitive adhesive layer of the present invention are liquid at ordinary temperature, have compatibility with the above-described acrylic copolymer and are uniformly distributed in the pressure-sensitive adhesive layer. As a result, these components show a function to plasticize the pressure-sensitive adhesive layer, thereby rendering possible addition of softness to the pressure-sensitive adhesive layer and reduction of pain and skin irritation caused by the skin adhesive force when the percutaneous absorption preparation of the present invention is removed from the skin surface. In addition, since the pressure-sensitive adhesive layer is plasticized as described above, free diffusion of ISDN contained therein becomes appropriate and its release to the skin surface (skin transfer property) is also improved.

In consequence, all types of fatty acid esters and monoglycerides at least having a function to plasticize the pressure-sensitive adhesive layer can be used in the present invention, but those comprising fatty acids having too many or too little carbon atoms have poor compatibility with the above-described acrylic copolymer and vaporize during a heating step of the production process of the preparation. Also, a fatty acid ester or a monoglyceride which comprises a fatty acid having a double bond in the molecule causes oxidation decomposition and the like, thus entailing poor preservation stability. In addition, in the case of an ISDN-containing preparation like the preparation of the present invention, crystals of ISDN exceeding its saturated solubility are formed in the preparation when the ISDN content per unit area is large, and certain types of fatty acid esters and monoglycerides inhibit crystallization of ISDN or delay its crystallization rate, thus causing a poor appearance of the resulting preparation or exerting a bad influence upon its preservation stability.

Therefore, a fatty acid ester comprising a higher fatty acid having 12 to 16, preferably 12 to 14, carbon atoms and a lower monohydric alcohol having 1 to 4 carbon atoms is used as the fatty acid ester of the present invention. Preferred examples of such a higher fatty acid include lauric acid (C12), myristic acid (C14) and palmitic acid (C16), of which myristic acid is more preferred. Examples of the lower monovalent alcohol which can be used include methyl alcohol, ethyl alcohol, propyl alcohol and butyl alcohol, which may be either straight-chain or branched alcohols. Isopropyl alcohol is more preferably used. Consequently, the most preferred fatty acid ester is isopropyl myristate.

On the other hand, a monoglyceride comprising a higher fatty acid having 8 to 10 carbon atoms and glycerol is used as the monoglyceride of the present invention. Preferred examples of such a higher fatty acid include caprylic acid (octanoic acid, C8), pelargonic acid (nonanoic acid, C9) and capric acid (decanoic acid, C10), of which caprylic acid is more preferred. Consequently, the most preferred monoglyceride is caprylic acid monoglyceride.

According to the percutaneous absorption preparation of the present invention, the fatty acid ester and the monoglyceride are used in a total amount of from 60 to 200 parts by weight, and preferably from 70 to 180 parts by weight, per 100 parts by weight of the acrylic copolymer. Blending ratio of the fatty acid ester to the monoglyceride is in the range of from 1:0.05 to 1:0.25, preferably from 1:0.065 to 1:0.24, and more preferably from 1:0.08 to 1:0.18. In this connection, it is desirable that each of the fatty acid ester and the monoglyceride used has a high purity of 85% or more, because changes in the above blending ratio exert influence upon the effects of the present invention extremely delicately.

If the total content and blending ratio of the fatty acid ester and monoglyceride are outside the above ranges, practical skin adhesion and low skin irritation cannot be obtained and release of ISDN (skin transfer) becomes insufficient. These problems become frequent as the size (area) of the percutaneous absorption preparation as a final product becomes small.

The pressure-sensitive adhesive layer of the percutaneous absorption preparation of the present invention is produced by blending ISDN as the drug for percutaneous absorption with the acrylic copolymer, fatty acid ester and monoglyceride as the essential components and making the mixture into a gel form by an appropriate crosslinking means, thereby preventing the outflow of the liquid components contained therein such as fatty acid ester, monoglyceride and the like and imparting cohesive force to the pressure-sensitive adhesive layer. The crosslinking reaction is effected by physical crosslinking means by irradiation with a radiation such as ultraviolet rays, electron rays or the like or by chemical crosslinking means using a crosslinking agent such as a polyisocyanate compound, an organic peroxide, an organometal salt, a metal alcoholate, a metal chelate compound, a polyfunctional compound or the like. When a radiation irradiation or an organic peroxide is used as the crosslinking means, decomposition reaction occurs under certain conditions. On the Other hand, where highly reactive isocyanate compounds, usually used metal salts or organic metal salts are used, coating workability in preparing the pressure-sensitive adhesive layer becomes poor in some cases because of the increment of solution viscosity after blending. Alternatively, a polyfunctional monomer such as a diacrylate may be copolymerized by blending it in advance at the time of the preparation of the acrylic copolymer, but such a method will also increase the solution viscosity at the time of polymerization. Therefore, a trifunctional isocyanate, a metal alcoholate comprising titanium or aluminium or a metal chelate compound is preferably used in the present invention from the standpoint of reactivity and easy handling. These crosslinking agents are markedly excellent in workability, because they do not cause increment of solution viscosity until coating and drying. The crosslinking agent is used in an amount of approximately from 0.01 to 2.0 parts by weight per 100 parts by weight of the acrylic copolymer.

The pressure-sensitive adhesive layer of the percutaneous absorption preparation of the present invention contains ISDN as the drug for percutaneous absorption. The ISDN content in the pressure-sensitive adhesive layer can appropriately be determined according to the purpose of administration and subjects to be administered, but is generally in the range of from 2 to 50% by weight, and preferably from 10 to 40% by weight. If the content of ISDN is smaller than 2% by weight, release of effective amount of ISDN is not expected, and if the content thereof is larger than 50% by weight, the proportionally increased effect cannot appear, which is not only economically disadvantageous, but also rather entails poor skin adhesion. However, ISDN may be blended in an amount exceeding its saturated solubility in the pressure-sensitive adhesive layer disregard of the above range, when it is necessary to add sustained release property for a prolonged period of time or to increase the releasing amount or miniaturize the preparation by increasing its content per unit area. From the practical point of view in relation to the fatty acid ester and monoglyceride, it is most preferred to include ISDN in the pressure-sensitive adhesive layer in an amount of approximately from 17 to 23% by weight.

As described above, the percutaneous absorption preparation of the present invention comprises a construction such that a crosslinked pressure-sensitive adhesive layer contains ISDN as a drug for percutaneous absorption, and as base materials for supporting ISDN, an acrylic copolymer, and specified fatty acid and monoglyceride which have compatibility with the copolymer. As a result, the pressure-sensitive adhesive layer is provided with softness while keeping its cohesive force, so that the preparation hardly causes either irritation during its application to the skin surface or skin irritation caused by damage to the corneous cells in the applied area of the skin when the preparation is removed. Because of this, markedly good balance of its pressure-sensitive characteristics and low skin irritation can be obtained and excellent pharmacological effects can be expected. In this connection, when quantity of corneous separation at the time of the removal of the percutaneous absorption preparation of the present invention from the skin surface of volunteers was analyzed using a spectrophotometer as an-index of painless removal of the preparation from the skin surface, the quantity of corneous separation caused by the preparation of the present invention was found to be ⅕ to ⅔ of that of a comparative preparation containing no fatty acid ester and monoglyceride, thus clearly showing advantages of the preparation of the present invention in pains and skin adhesion in removing.

In addition, since the pressure-sensitive adhesive layer of the percutaneous absorption preparation of the present invention is a so-called gel structure, diffusion transfer of ISDN contained therein has a large degree of freedom and its release therefore becomes good. What is more, since the blending of the monoglyceride renders possible excellent adhesion of the preparation to the irregular skin surface, the skin adhesion area increases and the release of ISDN (skin transfer) is improved while maintaining the skin adhesion.

The present invention is described in more detail by reference to the following examples, but it should be understood that the invention is not construed as being limited thereto. Unless otherwise indicated, all percents, parts, ratios and the like are by weight.

<Preparation of acrylic copolymer>

In an atmosphere of an inert gas, 95 parts of 2-ethylhexyl acrylate and 5 parts of acrylic acid were copolymerized in ethyl acetate to obtain an acrylic copolymer solution.

EXAMPLES 1 TO 4 AND COMPARATIVE EXAMPLES 1 TO 11

Viscous solutions of compositions for forming pressure-sensitive adhesive layers were prepared using the formulations shown in Table 1 below, and each of the thus prepared solutions was coated on a polyester separator (75 μm in thickness) in such an amount that the film layer when dried became 60 μm in thickness, and then dried to obtain a pressure-sensitive adhesive layer. The thus obtained pressure-sensitive adhesive layer was applied to the non-woven fabric side of a laminate film made of a polyester non-woven fabric (basis weight: 8 g/m$^2$) and a polyester film (2 μm in thickness).

Where pressure-sensitive adhesive compositions contained a crosslinking agent in an amount of 0.15 part per 100 parts by weight of the solid content of the acrylic copolymer, the compositions were applied to a non-woven fabric side as above and then aged at 70° C. for 60 hours under heating.

Each of the thus obtained tape-shaped percutaneous absorption preparations was cut into a predetermined size and allowed to stand at room temperature for 24 hours to precipitate crystals of ISDN as the drug for percutaneous absorption such that the crystals almost uniformly contained in the pressure-sensitive adhesive layer.

TABLE 1

| | Acrylic polymer (%) | ISDN (%) | Fatty acid ester (%) | Mono-glyceride (%) | Cross-linking agent | Remarks |
|---|---|---|---|---|---|---|
| Example 1 | 40 | 20 | IPM 37 | GMC 3 | C/HL | |
| Example 2 | " | " | IPM 35 | GMC 5 | " | |
| Example 3 | 43 | " | IPM 33 | GMC 4 | " | |
| Example 4 | 28 | " | IPM 45 | GMC 7 | " | |
| Comparative Example 1 | 40 | " | IPM 40 | — | " | |
| Comparative Example 2 | 30 | " | IPM 50 | — | " | |
| Comparative Example 3 | 35 | " | OP 40 | GMC 5 | " | |
| Comparative Example 4 | " | " | MITD 40 | GMC 5 | " | |
| Comparative Example 5 | " | " | OE 40 | GMC 5 | " | |
| Comparative Example 6 | " | " | IPM 40 | GMO 5 | " | |
| Comparative Example 7 | " | " | IPM 40 | GML 5 | " | |
| Comparative Example 8 | 80 | " | — | — | — | |
| Comparative Example 9 | 65 | " | IPM 12 | GMC 3 | C/HL | |
| Comparative Example 10 | 40 | " | IPM 37 | GMC 3 | — | Cohesive failure |
| Comparative Example 11 | PIB 80 | " | — | — | — | |

PIB: Polyisobutylene pressure-sensitive adhesive
viscosity average molecular weight 990,000;  10 parts
viscosity average molecular weight 60,000;  15 parts
viscosity average molecular weight 1,260;  3 parts
plus
alicyclic petroleum resin:  7 parts
(softening point, 100° C.)
ISDN: isosorbide dinitrate
Fatty acid esters: IPM (isopropyl myristate)
OP (octyl palmitate)
MITD (isotridecyl myristate)
OE (ethyl oleate)
Monoglycerides: GMC (glyceryl monocaprylate)
GMO (glyceryl monooreate)
GML (gryceryl monolaurate)
Crosslinking agent: C/HL (CORONATE HL: a trifunctional isocyanate, manufactured by Nippon Polyurethane Co.)

The percutaneous absorption preparations obtained in the above Examples and Comparative Examples were subjected to the following stability test. The results obtained are shown in Table 2 below. The preparation obtained in Comparative Example 10 was not able to be used in the stability test, because it caused cohesive failure due to lack in cohesive force of its pressure-sensitive adhesive layer.

<Stability test>

Each sample was sealed using a packaging material and stored at 40° C. under a moisture condition of 75% RH to measure the drug content (per unit area) after 1, 3 and 6 months of the storage. The content after storage (%) was calculated based on the initial content (100%). In this test, appearance of the surface of each sample, namely condition of formed ISDN crystals, was visually observed, and samples showing clearly irregular crystal formation were excluded from other tests.

TABLE 2

| | Content stability | | | Appearance stability | | |
|---|---|---|---|---|---|---|
| | 1 month (%) | 3 months (%) | 6 months (%) | 1 month | 3 months | 6 months |
| Example 1 | 100.4 | 99.9 | 100.2 | A | A | A |
| Example 2 | 100.0 | 100.1 | 100.0 | A | A | A |
| Example 3 | 99.8 | 99.9 | 100.1 | A | A | A |
| Example 4 | 100.2 | 100.0 | 99.7 | A | A | A |
| Comparative Example 1 | 100.5 | 99.9 | 100.1 | A | A | A |
| Comparative Example 2 | 100.0 | 100.2 | 99.9 | A | A | A |
| Comparative Example 3 | 99.6 | 100.1 | 99.8 | A | A | B |
| Comparative Example 4 | 100.1 | 100.2 | 100.3 | C | D | D |
| Comparative Example 5 | 99.0 | 98.1 | 95.3 | A | C | C |
| Comparative Example 6 | 98.1 | 96.5 | 93.8 | A | A | A |
| Comparative Example 7 | 99.9 | 99.8 | 100.0 | A | B | B |
| Comparative Example 8 | 100.2 | 100.1 | 100.2 | A | A | A |
| Comparative Example 9 | 100.0 | 99.8 | 99.8 | A | A | A |
| Comparative Example 11 | 100.0 | 99.8 | 100.2 | A | A | A |

Appearance stability (good ← A >B >C >D → bad)
A: No change in appearance (no change in formed crystals)
B: Formed crystals show light and shade (mottles)
C: Formed crystals become thin
D: Presence of a portion with no crystal formation As is apparent from the results shown in Table 2 above, samples in Comparative Examples 3 to 7 are inferior in either the content stability or the appearance stability. Next, the following tests were carried out using samples in Examples 1 to 4 and Comparative Examples 1, 2, 8, 9 and 11, which were relatively stable in the stability test. The results obtained are shown in Table 3 below.

<Adhesive force test>

Each sample cut into a tape-like shape of 24 mm in width was applied to a bakelite plate, closely contacted by adding 300 g of load with one reciprocation of a roller and then stripped off in a 180 degree direction at a rate of 300 mm/min to measure its adhesive force (peeling strength).

<Skin adhesive force test>

Each sample cut into a shape of 12 mm in width and 50 mm in length was applied to the inner part of the lower arm of each of five volunteers for 6 hours and then stripped off in a 180 degree direction at a rate of 100 mm/min to measure its skin adhesive force (peeling strength).

In this test, peeled removal of corneous cells was hardly found in samples of the Examples. On the other hand, each sample of Comparative Examples caused peeling of corneous cells, clearly showing that the interlaminar strength between corneous cells was smaller than the interfacial adhesive force. In consequence, the value of each Comparative Example shown in Table 3 is the interlaminar strength between corneous cells.

<Amount of corneum peeled>

Each sample cut into a shape of 12 mm in width and 50 mm in length was applied to the inner part of the lower arm of each of five volunteers for 6 hours and then stripped off. The resulting sample was soaked for 24 hours in the following dyeing solution and then washed with distilled water to carry out dyeing of the peeled corneous cells. Since the dyeing solution used in this test permeates into the backing-constituting non-woven fabric, the backing was replaced by a single layer of a polyester film having a thickness of 9 μm.

| Dyeing solution composition: | Gentian violet | 1.0% |
|---|---|---|
| | Brilliant Green | 0.5% |
| | Distilled water | 98.5% |

Each of the thus dyed samples was cut into a size of 12 mm×5 mm and dipped in 5 ml of 1% sodium dodecyl sulfate aqueous solution for a whole day and night to extract the pigments from the adhered corneous cells, and absorbance (595 nm) of the extract was measured using a spectrophotometer. Each sample which was not applied to the skin surface was used as a control sample and subjected to the same extraction operation to calculate the absorbance as a differential spectrum between the control and test samples. Namely, higher measured absorbance indicates larger amount of peeled corneous cells.

In this test, a good correlation was found between the number of peeled corneous cells counted under a stereoscope and the absorbance described above.

<Degree of pain>

Each sample cut into a size of 5 cm² was applied to the inner part of the upper arm of each of five volunteers for 1 hour and then peeled off to measure degree of pain at the time of peeling. The degree of pain was evaluated based on the following criteria to obtain average values.

1: no pain
2: feel pain
3: slightly painful
4: painful
5: strongly painful

TABLE 3

| | Adhesive force (g) | Skin adhesive force (g) | Amount of corneum peeled (abs.) | Degree of pain |
|---|---|---|---|---|
| Example 1 | 108 | 41 | 0.46 | 1.0 |
| Example 2 | 110 | 42 | 0.39 | 1.0 |
| Example 3 | 103 | 48 | 0.53 | 1.2 |
| Example 4 | 99 | 36 | 0.32 | 1.0 |
| Comparative Example 1 | 97 | 26 | 0.44 | 1.2 |
| Comparative Example 2 | 95 | 22 | 0.39 | 1.0 |
| Comparative Example 8 | 740 | 49 | 1.45 | 3.4 |
| Comparative Example 9 | 960 | 58 | 1.30 | 4.0 |
| Comparative Example 11 | 1620 | 50 | 1.60 | 4.8 |

As is apparent from the results shown in Table 3, the samples of the present invention have proper adhesive force and cause smaller amount of corneous cells and degree of pain when peeled off. The samples of Comparative Examples, on the other hand, cause a large amount of peeled corneous cells and are painful when peeled off. In the case of the samples of Comparative Examples, the skin adhesive force does not signify adhesive force on the surface of the skin but indicates peeling strength, because these samples cause peeling of corneous cells from the skin surface, so that the measured values themselves are not so large.

On the basis of the test results shown in Table 3, samples in Comparative Examples 8, 9 and 11 showing large amount of peeled corneous cells were excluded, and samples in Examples 1 to 4 and Comparative Examples 1 and 2 showing relatively good results were used in the following rabbit adhesion test to measure blood level of ISDN. The results obtained are shown in Table 4.

<Rabbit adhesion test>

Each of the samples cut into a size of 40 cm² was adhered to a previously hair-clipped dorsal part of a rabbit, and blood samples were collected in 5 ml portions after 1.5, 2.5, 4, 6 and 8 hours, and the blood ISDN level was measured by a gas chromatography.

TABLE 4

| | Rabbit blood level test | | |
|---|---|---|---|
| | C Max (ng/ml) | T max (hr) | AUC (ng · hr/ml) |
| Example 1 | 339 | 1.5 | 2280 |
| Example 2 | 351 | 1.5 | 2310 |
| Example 3 | 316 | 1.5 | 2100 |
| Example 4 | 376 | 1.5 | 2440 |
| Comparative Example 1 | 271 | 2.5 | 1800 |
| Comparative Example 2 | 290 | 2.5 | 1960 |

As is apparent from the results shown in Table 4, ISDN is quickly absorbed and percutaneous absorption is improved by the samples of the present invention.

While the invention has been described in detail and with reference to specific embodiments thereof, it will be apparent to one skilled in the art that various changes and modifications can be made therein without departing from the spirit and scope thereof.

What is claimed is:

1. A percutaneous absorption preparation comprising a backing and a pressure-sensitive adhesive layer containing a drug for percutaneous absorption formed on one side of the backing, wherein the pressure-sensitive adhesive layer comprises an acrylic copolymer prepared by copolymerization of a monomer mixture comprising a (meth)acrylic acid alkyl ester and a functional monomer as the essential components, a fatty acid ester comprising a higher fatty acid having 12 to 16 carbon atoms and a lower monohydric alcohol having 1 to 4 carbon atoms, a monoglyceride comprising a higher fatty acid having 8 to 10 carbon atoms and glycerol, wherein the weight ratio of said fatty acid ester to said monoglyceride is from 1:0.05 to 1:0.25, wherein the higher fatty acid is selected from the group consisting of caprylic acid, pelargonic acid and capric acid, and isosorbide dinitrate as the drug for percutaneous absorption, in an amount in the range of 2 to 50% by weight, and wherein the pressure-sensitive adhesive layer is crosslinked, wherein the total content of said fatty acid ester and monoglyceride is from 60 to 200 parts by weight per 100 parts by weight of said acrylic copolymer.

2. The percutaneous absorption preparation as claimed in claim 1, wherein said backing is a porous film or a laminate of a porous film and a non-porous plastic film, and the pressure-sensitive adhesive layer is formed on the porous film side.

3. The percutaneous absorption preparation of claim 1, wherein the isosorbide dinitrate is in an amount in the range of 10 to 40% by weight.

4. The percutaneous absorption preparation of claim 1, wherein the total content of the fatty acid ester and monoglyceride is from 70 to 180 parts by weight.

* * * * *